(12) United States Patent
Weber et al.

(10) Patent No.: US 10,426,414 B2
(45) Date of Patent: Oct. 1, 2019

(54) SYSTEM FOR TRACKING AN ULTRASONIC PROBE IN A BODY PART

(71) Applicant: KONINKLIJKE PHILIPS N.V., Eindhoven (NL)

(72) Inventors: Frank Michael Weber, Hamburg (DE); Niels Nijhof, Utrecht (NL); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/777,863

(22) PCT Filed: Nov. 25, 2016

(86) PCT No.: PCT/EP2016/078756
§ 371 (c)(1),
(2) Date: May 21, 2018

(87) PCT Pub. No.: WO2017/089509
PCT Pub. Date: Jun. 1, 2017

(65) Prior Publication Data
US 2018/0333112 A1    Nov. 22, 2018

(30) Foreign Application Priority Data

Nov. 25, 2015   (EP) ..................... 15196173

(51) Int. Cl.
*A61B 6/00*   (2006.01)
*A61B 6/12*   (2006.01)
(Continued)

(52) U.S. Cl.
CPC .............. *A61B 6/12* (2013.01); *A61B 6/4417* (2013.01); *A61B 6/5211* (2013.01);
(Continued)

(58) Field of Classification Search
CPC ......... A61B 6/12; A61B 6/5247; A61B 6/547; G06T 7/344
See application file for complete search history.

(56) References Cited

U.S. PATENT DOCUMENTS 5,357,550 A    10/1994   Asahina
7,916,919 B2 *  3/2011   Zheng ................... A61B 6/503
                                          382/128
(Continued)

FOREIGN PATENT DOCUMENTS

JP       10137238 A    5/1998
JP     2007282974 A   11/2007
(Continued)

OTHER PUBLICATIONS

Haak, Alexander et al "Segmentation of Multiple Heart cavities in 3-D Transesophageal Ultrasound Images", IEEE Transactions on Ultrasonics, Ferroelectrics, and Frequency Control, vol. 62, No. 6, Jun. 2015, pp. 1179-1189.

(Continued)

*Primary Examiner* — Joseph M Santos Rodriguez

(57) ABSTRACT

The present invention relates to a system for tracking the position of an ultrasonic probe in a body part. It is described to acquire (110) an X-ray image of a portion of a body part within which an ultrasonic probe (20) is positioned. First geometrical positional information of the ultrasonic probe in the portion of the body part is determined (120), utilizing the X-ray image. At least one ultrasonic image comprising a part of a body feature with the ultrasonic probe is acquired (130), the acquiring (130) comprising acquiring (140) an ultrasonic image of the at least one ultrasonic image at a later time than a time of acquisition of the X-ray image. Second geometrical positional information of the ultrasonic probe in the body part at the later time is determined (150), comprising uti- (Continued)

lizing the first geometrical positional information and the at least one ultrasonic image comprising the part of the body feature.

16 Claims, 5 Drawing Sheets

(51) Int. Cl.
*A61B 8/08* (2006.01)
*A61B 8/12* (2006.01)
*A61B 8/00* (2006.01)
*G06T 7/33* (2017.01)
*G06T 7/73* (2017.01)
*G06T 17/00* (2006.01)
*G06T 19/20* (2011.01)

(52) U.S. Cl.
CPC .......... *A61B 6/5223* (2013.01); *A61B 6/5247* (2013.01); *A61B 6/547* (2013.01); *A61B 8/085* (2013.01); *A61B 8/0841* (2013.01); *A61B 8/0883* (2013.01); *A61B 8/12* (2013.01); *A61B 8/4245* (2013.01); *A61B 8/4263* (2013.01); *A61B 8/4416* (2013.01); *A61B 8/466* (2013.01); *A61B 8/483* (2013.01); *A61B 8/5215* (2013.01); *A61B 8/5261* (2013.01); *G06T 7/344* (2017.01); *G06T 7/75* (2017.01); *G06T 17/00* (2013.01); *G06T 19/20* (2013.01); *A61B 6/4441* (2013.01); *A61B 6/487* (2013.01); *G06T 2207/10116* (2013.01); *G06T 2207/10132* (2013.01); *G06T 2207/20212* (2013.01); *G06T 2207/30048* (2013.01); *G06T 2210/41* (2013.01); *G06T 2219/2016* (2013.01)

(56) References Cited

U.S. PATENT DOCUMENTS

| 2007/0276216 | A1* | 11/2007 | Beyar ...................... A61B 6/12 600/407 |
| 2011/0075912 | A1 | 3/2011 | Rieber |
| 2012/0245458 | A1 | 9/2012 | Gogin |
| 2012/0296202 | A1 | 11/2012 | Mountney |
| 2013/0279780 | A1* | 10/2013 | Grbic ................... A61B 5/0033 382/131 |
| 2013/0303907 | A1 | 11/2013 | Corl |

FOREIGN PATENT DOCUMENTS

| JP | 2013017870 A | 1/2013 |
| WO | 2014102718 A1 | 7/2014 |
| WO | 2014126955 A1 | 8/2014 |

OTHER PUBLICATIONS

Gao, Gang et al "Registration of 3D trans-esophageal Echocardiography to X-ray Fluoroscopy using Image-based Probe Tracking", Medical Image Analysis, vol. 16, 2012, pp. 38-49.

Ecabert, Olivier, et al, "Automatic Model-based Segmentation of the Heart in CT Images." IEEE Transactions on Medical Imaging, vol. 27, No. 9, Sep. 2008, pp. 1189-1201.

Housden, R. James et al "Extended-Field-of-View Three-Dimensional Transesophageal Echocardiography using Image-Based X-Ray Probe Tracking", Ultrasound in Medicine and Biology, vol. 39, No. 6, 2013. pp. 993-1005.

* cited by examiner

SYSTEM FOR TRACKING AN ULTRASONIC PROBE IN A BODY PART

CROSS-REFERENCE TO PRIOR APPLICATIONS

This application is the U.S. National Phase application under 35 U.S.C. § 371 of International Application No. PCT/EP2016/078756, filed on Nov. 26, 2016, which claims the benefit of European Patent Application No. 15196173.7, filed on Nov. 25, 2015. These applications are hereby incorporated by reference herein.

FIELD OF THE INVENTION

The present invention relates to a system for tracking the position of an ultrasonic probe in a body part, and to a method for tracking the position of an ultrasonic probe in a body part, as well as to a computer program element and a computer readable medium.

BACKGROUND OF THE INVENTION

Combined transoesophageal echo (TEE) and X-ray systems support interventional procedures. TEE utilizes an ultrasonic probe that is passed into a patient's oesophagus, and provides clear images because there is less signal attenuation with respect to transthoracial ultrasound imagery. This is particularly relevant for ultrasound imagery of the heart, because the heart is positioned close to the oesophagus. Currently in a combined TEE/X-ray system, the TEE probe is localized in the X-ray, with the TEE probe position and orientation determined from X-ray images. However the TEE probe cannot be tracked without the continuous acquisition of X-ray images or the use of additional tracking devices.

R. J. Housden et al., Ultrasound in Med. & Biol., Vol. 39, No. 6, pp. 993-1005, 2013, describe extended-field-of-view three-dimensional transesophageal echocardiography using image-based X-ray probe tracking.

SUMMARY OF THE INVENTION

It would be advantageous to have an improved technique for tracking the position of an ultrasonic probe in a body part.

The object of the present invention is solved with the subject matter of the independent claims, wherein further embodiments are incorporated in the dependent claims. It should be noted that the following described aspects of the invention apply also for the system for tracking the position of an ultrasonic probe in a body part, the workstation for tracking the position of an ultrasonic probe in a body part, the method for tracking the position of an ultrasonic probe in a body part, and for the computer program element and the computer readable medium.

According to a first aspect, there is provided a system for tracking the position of an ultrasonic probe in a body part, comprising:

an ultrasonic probe;
an X-ray image acquisition unit; and
a processing unit;

The X-ray image acquisition unit is configured to acquire an X-ray image of a portion of a body part within which the ultrasonic probe is positioned. The processing unit is configured to determine first geometrical positional information of the ultrasonic probe in the portion of the body part, comprising utilizing the X-ray image. The ultrasonic probe is configured to acquire at least one ultrasonic image comprising a part of a body feature, the at least one ultrasonic image comprising an ultrasonic image to be acquired at a later time than a time of acquisition of the X-ray image of the portion of the body part. The processing unit is also configured to determine second geometrical positional information of the ultrasonic probe in the body part at the later time, comprising utilizing the first geometrical positional information and the at least one ultrasonic image comprising the part of the body feature. Optionally, the system comprises an output unit that is configured to output data representative of the second geometrical positional information of the ultrasonic probe. In other words, the system does not have to output data because tracking can be effectively done by the processing unit itself based on the first and second geometrical positional information.

In other words, the position (location and orientation) of an ultrasonic probe in a body part can be determined from an X-ray image, and the relative position between the ultrasonic probe and a part of a body feature such as the heart can be determined from the X-ray image and/or an ultrasonic image. On the basis of a later ultrasonic image, the relative position between the ultrasonic probe and the part of the body feature can be determined, from which the new position (location and orientation) of the ultrasonic probe can be determined.

To put it another way, the system can track an ultrasound probe, for example a transoesophageal echo (TEE) ultrasonic probe, in a combined TEE/X-ray system. To put it another way, an ultrasound probe is tracked in an indirect manner, through ultrasound images themselves.

In this manner, an X-ray image can be used to determine the position of an ultrasonic probe in a body part, and determine the location and/or orientation of the probe with respect to the body part and features or parts of features within the body part, such as for example the heart. Then, an ultrasonic image acquired by the ultrasonic probe at a later time can be used to determine the relative position of the ultrasonic probe with respect to the body part and features or parts of features within the body part, such as the heart. Knowledge of the positional information as determined by the X-ray image, such as location and orientation, and the relative positional information as determined by the ultrasonic image acquired at the later time can be used to determine positional information, such as location and orientation of the ultrasonic probe, at the later time. In other words, by using at least one ultrasound image to track the position of the ultrasound probe rather than using X-ray images, the X-ray dosage is reduced and external tracking systems are not required. To put it another way, when the X-ray image acquisition unit is turned off, an indirect way using at least one ultrasound image acquired by an ultrasound probe and the last acquired X-ray image the position of the ultrasound probe can be tracked.

In an example, the at least one ultrasonic image comprising the part of the body feature comprises at least two ultrasonic images comprising the part of the body feature, wherein the ultrasonic probe is configured to acquire an ultrasonic image at substantially the same time as the time of acquisition of the X-ray image of the portion of the body part. In other words, the processing unit, comprising utilizing the first geometrical positional information and the ultrasonic image comprising the part of the body feature acquired at substantially the same time as the acquisition of the X-ray image and the ultrasonic image of the part of the body feature acquired at the later time than the time of acquisition of the X-ray image, is configured to determine the second geometrical positional information of the ultrasonic probe in the body part at the later time.

In this manner, an X-ray image can be used to determine the position of an ultrasonic probe in a body part. An ultrasonic image of a body feature or part of a body feature acquired at substantially the same time provides information on the relative position between the ultrasonic probe and the part of body feature acquired from a known location. Then a subsequent ultrasonic image of the body feature, or part of the body feature, provides information on the relative position between the ultrasonic probe and the body feature acquired from a different position, such as a different location and/or orientation. Changes in the ultrasonic image of the body feature between the two ultrasonic images can be used to determine a change in position of the ultrasonic probe in terms of a change in location and/or orientation. By referencing back to the original known location and/or orientation, as determined by the X-ray image, a new location and/or orientation of the ultrasonic probe can be determined.

In other words, shifting and/or rotating the ultrasonic probe also shifts and/or rotates the position of the part of the body feature, such as the heart, in presently acquired ultrasonic image with respect to a previously acquired ultrasonic image. This enables the current probe location and/or orientation (or rotational position) to be estimated. In an example, movements of the part of the body feature, such as the heart, can be ignored in a first approximation, or are eliminated or reduced. In this way, the estimated ultrasonic probe location and/or orientation gives a radiation free approximation of the ultrasonic probe's real position.

In other words, by determining a location and orientation of the ultrasonic probe, from an X-ray image, whilst at the same time acquiring an ultrasonic image with the ultrasonic probe, enables global and anatomical contextual and spatial information to be determined.

In this manner, the ultrasonic probe can be continuously tracked without the need for continuous X-ray dose exposure or the need to use additional tracking devices.

In an example, the X-ray image acquisition unit is configured to acquire a second X-ray image of the portion of the body part within which the ultrasonic probe is positioned if the processing unit determines that a threshold value has been exceeded as a function of the first geometrical positional information and the second geometrical positional information.

In other words, if the location in terms of x, y, and y coordinates, and/or the angular rotation (or orientation) of the ultrasonic probe has changed by more than a threshold level since that determined by a previous X-ray image, a new X-ray image is acquired in order to provide an accurate determination of the location and/or orientation of the ultrasonic probe.

To put it another way, the location and/or orientation of the ultrasonic probe determined on the basis of the ultrasonic imagery itself can be augmented by an X-ray image, when a threshold in movement has been reached. The threshold could indicate that the estimated location and/or orientation of the ultrasonic probe may be susceptible to errors, and the acquisition of an X-ray image then serves to provide the precise location and/or orientation of the ultrasonic probe. The location and/or orientation of the ultrasonic probe can then be tracked using the at least one ultrasonic image and this means that the number of X-ray images acquired can be minimized, reducing the X-ray dose and without additional tracking equipment being used, whilst the ultrasonic probe's location and/or orientation can be tracked.

In an example, the processing unit is configured to determine at least one position of the ultrasonic probe relative to at least one position of the part of the body feature by utilizing the at least one ultrasonic image, and wherein the processing unit being configured to determine the second geometrical positional information of the ultrasonic probe comprises utilizing the at least one position of the ultrasonic probe relative to the at least one position of the part of the body feature.

In an example, the processing unit is configured to determine segmented data of the part of the body feature using model based segmentation by utilizing the at least one ultrasonic image comprising the part of the body feature, and wherein the processing unit being configured to determine the second geometrical positional information of the ultrasonic probe comprises utilizing the segmented data of the part of the body feature.

To put it another way, the part of the body feature as determined from an ultrasonic image can be located within the patient's body where use is made of an X-ray image of the body.

In an example, the processing unit is configured to determine a position of the part of the body feature as a reference position by utilizing the at least one ultrasonic image comprising the part of the body feature, and wherein the processing unit being configured to determine the second geometrical positional information of the ultrasonic probe comprises utilizing the reference position of the part of the body feature.

In this manner, relative movement between the ultrasonic probe and the part of the body feature that is not due to movement of the ultrasonic probe can be accounted for, and this enables the location and/or orientation of the ultrasonic probe due to movement of the ultrasonic probe to be determined.

In an example, the processing unit being configured to determine the first geometrical positional information of the ultrasonic probe in the portion of the body part comprises utilization of a three dimensional model of the ultrasonic probe.

In an example, the processing unit is configured to compare a projection of the three dimensional model of the ultrasonic probe with the X-ray image.

In an example, the processing unit is configured to iteratively determine a similarity between the three dimensional model and the X-ray image utilizing an image comparison metric.

In an example, the processing unit is configured to optimize a position and/or orientation of the three dimensional model by maximizing the image comparison metric.

In an example, wherein the processing unit is configured to compare the three dimensional model with the X-ray image comprising adjustment of at least one translational degree of freedom of the three dimensional model and/or adjustment of at least one rotational degree of freedom of the three dimensional model.

In a second aspect, there is provided a workstation for tracking the position of an ultrasonic probe in a body part, comprising:

at least one input unit; and a processing unit.

The at least one input unit is configured to provide an X-ray image of a portion of a body part within which an ultrasonic probe was positioned. The processing unit is configured to determine first geometrical positional information of the ultrasonic probe in the portion of the body part, comprising utilizing the X-ray image. The at least one input unit is also configured to provide at least one ultrasonic image comprising a part of a body feature, wherein the at least one ultrasonic image was acquired by the ultrasonic probe and wherein an ultrasonic image was acquired at a later time than a time of acquisition of the X-ray image of the portion of the body part. The processing unit is also configured to determine second geometrical positional information of the ultrasonic probe in the body part at the later time, comprising utilizing the first geometrical positional information and the at least one ultrasonic image comprising the part of the body feature. Optionally, the workstation comprises an output unit that is configured to output data representative of the second geometrical positional information of the ultrasonic probe.

In other words, the workstation can track the position of an ultrasonic probe on the basis of pre-acquired imagery. In this manner, the position of an ultrasonic probe in a body part can be checked or validated to ensure that it was correctly positioned at a particular point in time. Furthermore, the workstation can be used for training purposes.

In a third aspect, there is provided a method for tracking the position of an ultrasonic probe in a body part, comprising:

a) acquiring an X-ray image of a portion of a body part within which an ultrasonic probe is positioned;
b) determining first geometrical positional information of the ultrasonic probe in the portion of the body part, comprising utilizing the X-ray image;
c) acquiring at least one ultrasonic image comprising a part of a body feature with the ultrasonic probe, comprising acquiring an ultrasonic image at a later time than a time of acquisition of the X-ray image; and
g) determining second geometrical positional information of the ultrasonic probe in the body part at the later time, comprising utilizing the first geometrical positional information and the at least one ultrasonic image comprising the part of the body feature.

In an example, the method comprises:
i) outputting of data representative of the second geometrical positional information of the ultrasonic probe.

In an example, step c) comprises acquiring at least two ultrasonic images comprising the part of the body feature with the ultrasonic probe, and step c) further comprises acquiring an ultrasonic image at substantially the same time as the time of acquisition of the X-ray image of the portion of the body part.

In an example, step c) comprises acquiring at least two ultrasonic images comprising the part of the body feature with the ultrasonic probe, and step c) further comprises acquiring an ultrasonic image at substantially the same position as a position of the ultrasonic probe when the X-ray image of the portion of the body part was acquired.

In other words, the easiest way to acquire an ultrasound image at the same position as a position of the ultrasound probe when the X-ray image was acquired is to acquire the ultrasound image at the same time as acquiring the X-ray image, but this is not the only way of doing this.

In an example, the method comprises:
h) acquiring a second X-ray image of the portion of the body part within which the ultrasonic probe is positioned if a threshold has been exceeded as a function of the first geometrical positional information and the second geometrical positional information.

In an example, the method comprises:
d) determining at least one position of the ultrasonic probe relative to at least one position of the part of the body feature, utilizing the at least one ultrasonic image; and
wherein step g) comprises utilizing the at least one position of the ultrasonic probe relative to the at least one position of the part of the body feature.

In an example, the method comprises:
e) determining segmented data of the part of the body feature using model based segmentation, utilizing the at least one ultrasonic image comprising the part of the body feature; and
wherein step g) comprises utilizing the segmented data of the part of the body feature.

In an example, the method comprises:
f) determining a position of the part of the body feature as a reference position, utilizing the at least one ultrasonic image comprising the part of the body feature; and
wherein step g) comprises utilizing the reference position of the part of the body feature.

In an example, phase alignment can be conducted to account for motion of the heart. This means that phases are aligned between ultrasound images, in that the heart phase for a subsequent ultrasound image should be the same as that for an earlier ultrasound image.

According to another aspect, there is provided a computer program element controlling apparatus (i.e., the system and workstation) as previously described which, in the computer program element is executed by processing unit, is adapted to perform the method steps as previously described.

According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
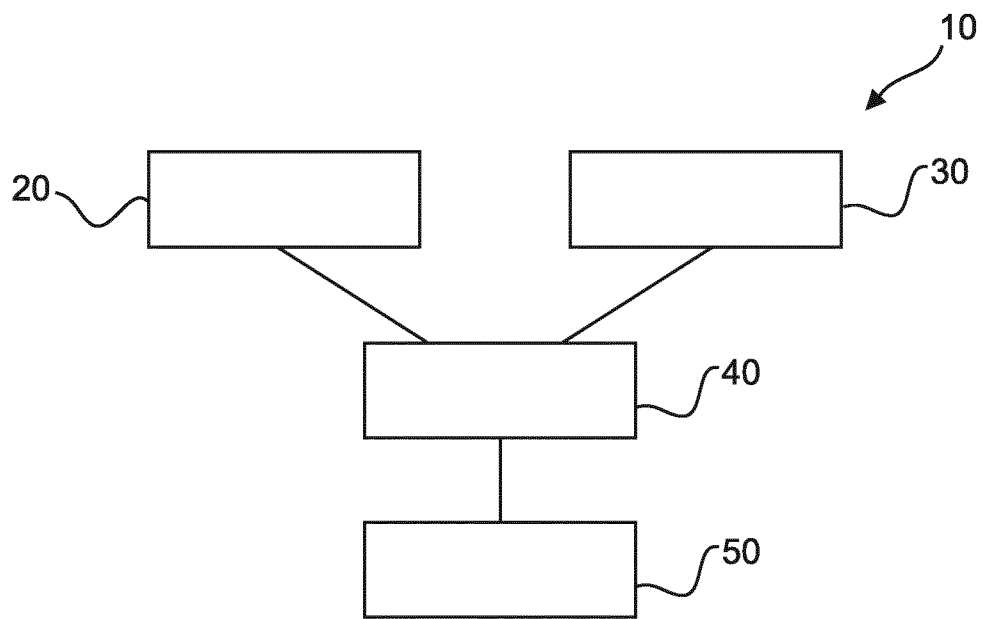
FIG. 1 shows a schematic set up of an example of a system for tracking the position of an ultrasonic probe in a body part.

FIG. 1 shows an example of a system 10 for tracking the position of an ultrasonic probe in a body part. The system 10 comprises an ultrasonic probe 20, an X-ray image acquisition unit 30, a processing unit 40, and optionally comprises an output unit 50. The X-ray image acquisition unit 30 is configured to acquire an X-ray image of a portion of a body part within which the ultrasonic probe 20 is positioned, which is provided to the processing unit 40. The processing unit 40 is configured to determine first geometrical positional information of the ultrasonic probe in the portion of the body part, comprising utilizing the X-ray image. The ultrasonic probe 20 is configured to acquire at least one ultrasonic image comprising a part of a body feature, the at least one ultrasonic image comprising an ultrasonic image to be acquired at a later time than a time of acquisition of the X-ray image of the portion of the body part. The processing unit 40 is also configured to determine second geometrical positional information of the ultrasonic probe in the body part at the later time, comprising utilizing the first geometrical positional information and the at least one ultrasonic image comprising the part of the body feature. The output unit is configured to output data representative of the second geometrical positional information of the ultrasonic probe.

In an example, the ultrasonic probe is a transoesophageal echo (TEE) ultrasonic probe. In an example, the ultrasonic probe comprises a transducer encapsulated in a rigid head. In an example, the "ultrasonic probe" means the rigid encapsulated head.

In an example, the X-ray image acquisition unit comprises a C-arm CT system. In an example, the image acquisition unit comprises an interventional X-ray system.

In an example, the X-ray image of the portion of the body part comprises fluorescence image data. In an example, the image acquisition unit comprises fluoroscopic X-ray equipment. In an example, the X-ray image of the portion of the body part was acquired during fluoroscopic low-dose X-ray surveillance. In an example, fluoroscopic low-dose X-ray surveillance is used to determine the first geometrical positional information of the ultrasonic probe in the portion of the body part.

In an example, the X-ray image of the body part comprises the part of the body feature.

In an example, the first geometrical positional information of the ultrasonic probe in the portion of the body part comprises a location of the ultrasonic probe. In an example, the location comprises x, y, and z coordinates of the ultrasonic probe, or a part of the ultrasonic probe. In an example, the x, y, and z coordinates of the ultrasonic probe, or part of the ultrasonic probe, relate to a reference point, such as a part or point of a medical table or a part or point of the X-ray image acquisition unit. In an example, the first geometrical positional information of the ultrasonic probe in the body part comprises an orientation of the ultrasonic probe, or a part of the ultrasonic probe. In an example, the orientation comprises an angular position of the ultrasonic probe or a part of the ultrasonic probe about its longitudinal axis, for example the angular position of an axis, extending from the longitudinal axis through the center of an output window, about the longitudinal axis with respect to a vertical direction or axis. In an example, the orientation comprises the three rotation angles (Euler angles or roll-pitch-yaw angles) to align the ultrasonic probe coordinate system with the X-ray image acquisition unit or coordinate system of the medical table.

In an example, determining first geometrical positional information of the ultrasonic probe in the portion of the body part comprises 2D-3D registration of the X-ray image. In an example, 2D-3D registration comprises determining a 3D model of the ultrasonic probe. In an example, 2D-3D registration comprises registering the 3D model of the ultrasonic probe to the X-ray image using a 2D-3D image registration algorithm. In an example, 2D-3D registration comprises positioning the 3D model of the ultrasonic probe within the coordinate system of the X-ray unit or medical table, and comparing a modeled projection of the 3D ultrasonic probe with the X-ray image that details the actual projection of the ultrasonic probe within the coordinate system of the X-ray unit or medical table. In an example, the 3D model of the ultrasonic probe is repeatedly repositioned unit the modeled X-ray projection of the ultrasonic probe matches the actual acquired projection of the ultrasonic probe. In this manner, the location and orientation of the ultrasonic probe can be determined both with respect to the coordinate system of the X-ray unit or medical table and determined with respect to the body part. In this manner, because the ultrasonic probe has a known field of view from the location and orientation of the ultrasonic probe determined from the X-ray image, the field of view of the ultrasonic probe with respect to the body part can be determined. In other words, the region of the body that the ultrasonic probe is looking at can be determined. To put it another way, the volume of body space that the ultrasonic probe is interrogating can be located in the X-ray image.

In an example, the region of the body part is a region of the portion of the body part.

In an example, the second geometrical positional information of the ultrasonic probe in the body part relates to the ultrasonic probe being positioned within the portion of the body part. In an example, the second geometrical positional information of the ultrasonic probe in the body part comprises a location of the ultrasonic probe. In an example, the location comprises x, y, and z coordinates of the ultrasonic probe, or a part of the ultrasonic probe. In an example, the x, y, and z coordinates of the ultrasonic probe relate to a reference point, such as a part or point of a medical table or a part or point of the X-ray image acquisition unit. In an example, the second geometrical positional information of the ultrasonic probe in the body part comprises an orientation of the ultrasonic probe. In an example, the orientation comprises an angular position of a part of the ultrasonic probe about its longitudinal axis, for example the angular position of an output window about the longitudinal axis with respect to a vertical direction. In an example, the second geometrical positional information of the ultrasonic probe relates to the ultrasonic probe being at a different location to the location of the ultrasonic probe with respect to the first geometrical positional information. In an example, the second geometrical positional information for the ultrasonic probe relates to the ultrasonic probe being at a different orientation to the orientation of the ultrasonic probe with respect to the first geometrical positional information. In an example, the second geometrical positional information for the ultrasonic probe relates to the ultrasonic probe being at the same location to the location of the ultrasonic probe with respect to the first geometrical positional information, but having a different orientation to the orientation of the ultrasonic probe with respect to the first geometrical positional information. In an example, the second geometrical positional information for the ultrasonic probe relates to the ultrasonic probe being at different location to the location of the ultrasonic probe with respect to the first geometrical positional information, but having the same orientation to the orientation of the ultrasonic probe with respect to the first geometrical positional information. In an example, the second geometrical positional information for the ultrasonic probe relates to the ultrasonic probe being at a different location to the location of the ultrasonic probe with respect to the first geometrical positional information, and having a different orientation to the orientation of the ultrasonic probe with respect to the first geometrical positional information.

In an example, the part of the body feature is detected in the at least one ultrasonic image. In an example, the position of the part of the body feature is determined within the field of view of the ultrasonic probe. In an example, the position of the part of the body feature is determined within the volume of space that the ultrasonic probe interrogating or is configured to interrogate within the body part. In an example, the part of the body feature is detected in the X-ray image. In an example, the position of the part of the body feature within the body is determined from the X-ray image. In other words, the position of the part of the body feature within the volume of body space that an ultrasonic probe is looking at can be determined from an ultrasonic image acquired by the ultrasonic probe and/or can be determined from an X-ray image.

In an example, the part of the body feature is the heart of a patient. In other words the part of the body features includes all of the body feature, which can be for example the heart. In an example, the body feature is the spine of a patient. In an example, the body feature can be any other part or organ of a patient than can be identified on the basis of acquired imagery.

In an example, the output unit is configured to output data representative of the X-ray image. In an example, the output unit is configured to output data representative of the at least one ultrasonic image. In an example, the output unit is configured to save data relating to any one of the X-ray image, the first geometrical positional information, the at least one ultrasound image, and the second geometrical positional information. In an example, the output unit is configured to display image data, for example displaying images on one or more monitors such as one or more visual display units VDUs. In an example, the output unit is configured to display the at least one ultrasonic image of the body feature. In an example, the output unit is configured to display an ultrasonic image of the body feature. In an example, the output unit is configured to display the X-ray image of the portion of the body part. In an example, the output unit is configured to display the X-ray image of the portion of the body part and the second geometrical positional information of the ultrasonic probe. In other words, the present location and/or orientation of the ultrasonic can be presented in an acquired X-ray image. To put it another way, in an example the current location and/or orientation of the ultrasonic probe can be shown as an overlay in the X-ray image of a portion of a body part. In other words, augmented visualization of the current probe position, determined from at least one ultrasonic image, can be provided on a static X-ray image acquired at an earlier point in time.

According to an example, the at least one ultrasonic image comprising the part of the body feature comprises at least two ultrasonic images comprising the part of the body feature. The ultrasonic probe is then configured to acquire an ultrasonic image at substantially the same time as the time of acquisition of the X-ray image of the portion of the body part.

According to an example, the X-ray image acquisition unit is configured to acquire a second X-ray image of the portion of the body part within which the ultrasonic probe is positioned. This is done if the processing unit determines that a threshold value has been exceeded as a function of the first geometrical positional information and the second geometrical positional information.

In an example, the processing unit determines if the threshold has been exceeded if the processing unit determines that a difference between the first geometrical positional information and the second geometrical positional information exceeds a threshold.

In an example, the X-ray image acquisition unit being configured to acquire a second X-ray image comprises a doctor or clinician being informed that a threshold has been exceeded, and the doctor or clinician can then trigger the acquisition of the second X-ray manually. In this manner, additional safety measures are provided with respect to X-ray dosage.

According to an example, the processing unit is configured to determine at least one position of the ultrasonic probe relative to at least one position of the part of the body feature by utilizing the at least one ultrasonic image. The processing unit being configured to determine the second geometrical positional information of the ultrasonic probe then comprises the processing unit utilizing the at least one position of the ultrasonic probe relative to the at least one position of the part of the body feature.

According to an example, the processing unit is configured to determine segmented data of the part of the body feature using model based segmentation by utilizing the at least one ultrasonic image comprising the part of the body feature. The processing unit being configured to determine the second geometrical positional information of the ultrasonic probe comprises the processing unit utilizing the segmented data of the part of the body feature.

In an example, from a current ultrasonic image, an estimate is made of the ultrasonic probe location and orientation relative to the segmented part of the body feature, for example the heart or part of the heart.

In an example, segmentation of the part of the body feature, e.g. heart, provides the outlines of the part of the body feature within the volume of space that the ultrasonic probe is looking at. In this manner, from the 2D-3D registration of the ultrasonic probe from the X-ray image which provided the position of the ultrasonic probe and also provided mapping of the volume of space that the ultrasonic probe is looking at to the body and to the X-ray image, the outline of the part of the body feature determined from the ultrasonic image can be drawn or overlaid onto the X-ray image.

In an example, the part of the body feature, for example the heart, is continuously segmented in the at least one ultrasonic images acquired by the ultrasonic probe. In an example, the segmentation adapts a mesh model to the ultrasonic image of the part of the body feature. In an example, the mesh structure does not change. In this manner, because the mesh structure does not change, corresponding points between different segmentation results across different ultrasonic images are known. In this way, shifting and/or rotation of the part of the body feature between different ultrasonic images can be determined from which the location and/or orientation of the ultrasonic probe can be determined.

According to an example, the processing unit is configured to determine a position of the part of the body feature as a reference position by utilizing the at least one ultrasonic image comprising the part of the body feature. The processing unit being configured to determine the second geometrical positional information of the ultrasonic probe comprises the processing unit utilizing the reference position of the part of the body feature.

In an example, determining the position of the part of the body feature as a reference position comprises eliminating movements of the part of the body feature. In an example, the determined position of the part of the body feature, e.g. heart, is used as a fixed reference.

In an example, the processing unit is configured to register the at least one ultrasonic images with respect to cardiac cycle, patient motion or patient breathing, or any combination thereof. In other words, for example the at least one ultrasonic images used to determine the location and/or orientation of the ultrasonic probe can relate to images acquired in the same or similar point within a patient's cardiac cycle, or at the same or similar point within a patient's breathing cycle. In an example, the processing unit is configured to register the at least one ultrasonic images and the X-ray image with respect to cardiac cycle, patient motion or patient breathing, or any combination thereof. In other words, for example the at least one ultrasonic images and the X-ray image used to determine the location and/or orientation of the ultrasonic probe can relate to images acquired in the same or similar point within a patient's cardiac cycle, or at the same or similar point within a patient's breathing cycle.

In an example, intrinsic heart motion can be excluded by analyzing a consistent heart phase, such as end-systole. In an example, analyzing a consistent heart phase comprises monitoring an electrocardiogram (ECG) signal. In an example, a patient's breathing cycle can be detected with a respiration belt, as similarly used for example in Magnetic Resonance (MR) imaging. In an example, analyzing a consistent heart phase comprises utilizing segmentation data, or in other words the intrinsic heart motion can be excluded by analyzing the segmentation result, for example when looking at the chamber volumes.

In this manner, by accounting for relative movement between the ultrasonic probe and the part of the body feature that is not due to movement of the ultrasonic probe, the location and/or orientation of the ultrasonic probe due to movement of the ultrasonic probe can be determined.

In an example, the X-ray image of the portion of the body part comprises X-ray image data of the part of the body feature, and wherein the processing unit being configured to determine second geometrical positional information of the ultrasonic probe in the body part at the later time comprises utilizing the X-ray image data of the part of the body feature. In an example, the position of the part of the body feature in the X-ray image is utilized.

Figure 2:
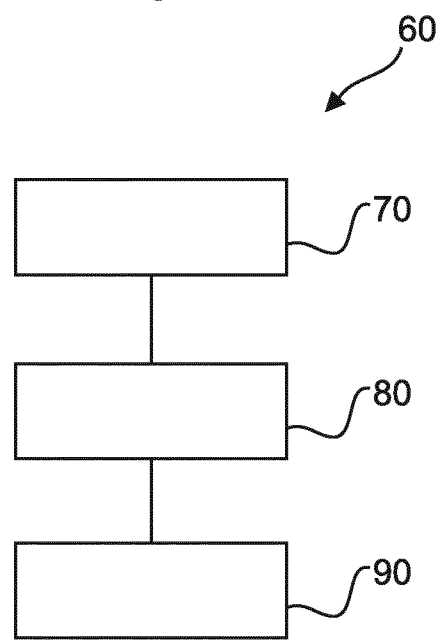
FIG. 2 shows a schematic set up of another example of a system for tracking the position of an ultrasonic probe in a body part.

FIG. 2 shows an example of a system 60 for tracking the position of an ultrasonic probe in a body part. The system 60 comprises: at least one input unit 70, a processing unit 80; and optionally an output unit 90. The at least one input unit 70 is configured to provide an X-ray image of a portion of a body part within which an ultrasonic probe 20 was positioned to the processing unit 80. The processing unit 80 is configured to determine first geometrical positional information of the ultrasonic probe in the portion of the body part, comprising utilizing the X-ray image. The at least one input unit 70 is configured to provide at least one ultrasonic image comprising a part of a body feature, wherein the at least one ultrasonic image was acquired by the ultrasonic probe 20 and wherein an ultrasonic image of the at least one ultrasonic image was acquired at a later time than a time of acquisition of the X-ray image of the portion of the body part. The processing unit 80 is also configured to determine second geometrical positional information of the ultrasonic probe in the body part at the later time, comprising utilizing the first geometrical positional information and the at least one ultrasonic image comprising the part of the body feature.

The output unit 90 is configured to output data representative of the second geometrical positional information of the ultrasonic probe.

In an example, the at least one input unit comprises a data storage or transfer unit configured to provide the X-ray image. In an example, an X-ray image acquisition unit is configured to acquire the X-ray image and this is provided to the data storage or transfer unit. In an example, the input unit comprises the X-ray acquisition unit. In an example, the at least one input unit comprises the ultrasonic probe.

In an example, the at least one input unit comprises a data storage or transfer unit configured to provide the at least one ultrasonic image, for example via a continuous feed. In this manner, an add on box to an existing X-ray/ultrasound system can be provided just for tracking purposes.

In an example, the ultrasound image acquired at the later time than the acquisition of the X-ray image comprises two orthogonal slices and the ultrasound image acquired at substantially the same time as the time of acquisition of the X-ray image comprises two orthogonal slices. In other words, ultrasound images can be acquired in x-plane mode, where two orthogonal slices are recorded and from which changes in the position of the part of the body feature, e.g. heart, can be tracked, enabling an updated ultrasonic probe location to be estimated. X-plane mode is faster than full 3D volume acquisition, whilst still enabling ultrasonic probe position changes to be estimated providing for tracking of the ultrasonic probe.

Figure 3:
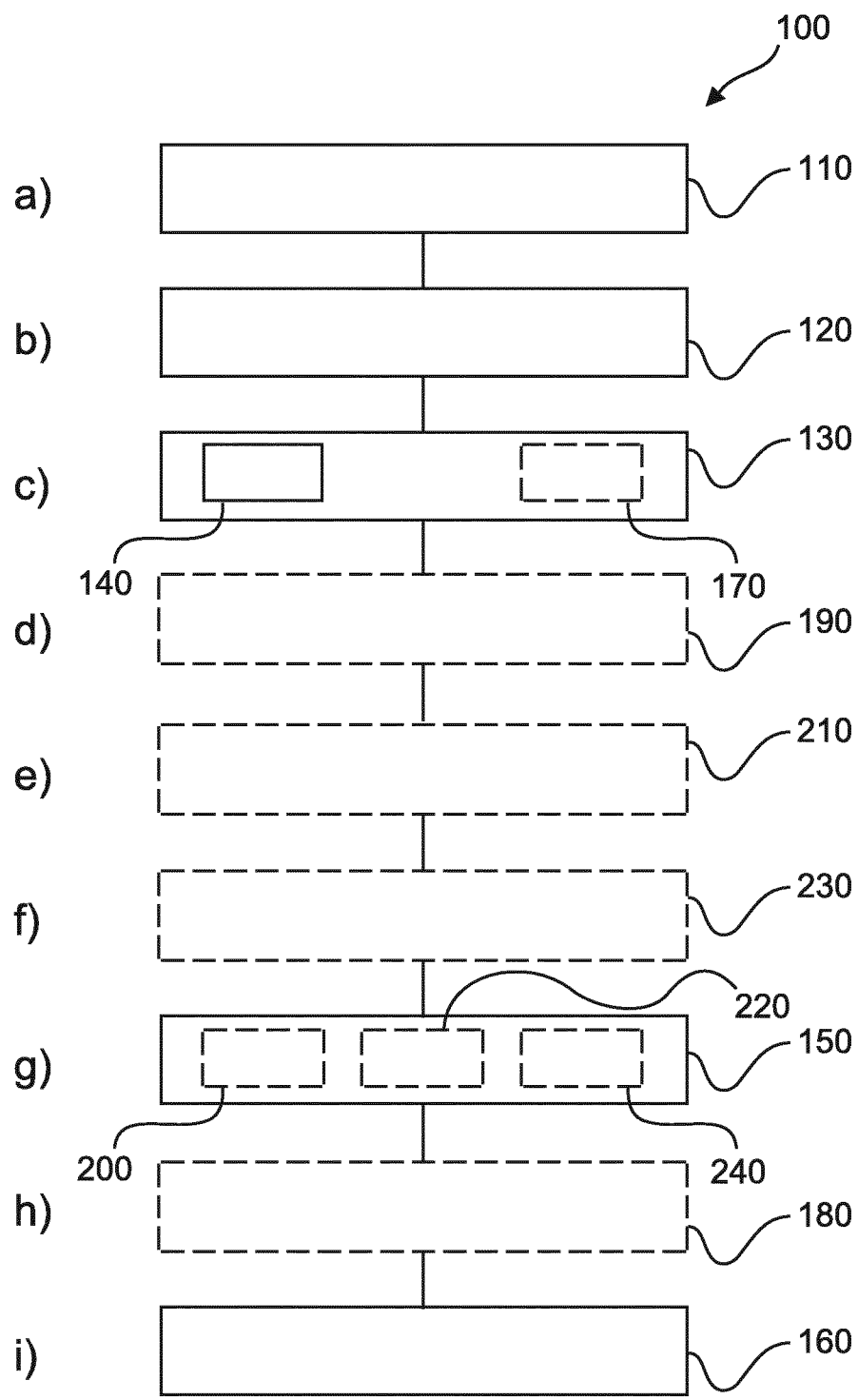
FIG. 3 shows an example of a method for tracking the position of an ultrasonic probe in a body part.

FIG. 3 shows a method 100 for tracking the position of an ultrasonic probe in a body part in its basic steps, except that the outputting of data is optional. The method comprises the following:

In a first acquiring step 110, also referred to as step a), an X-ray image of a portion of a body part within which an ultrasonic probe 20 is positioned is acquired.

In a first determining step 120, also referred to as step b), first geometrical positional information of the ultrasonic probe 20 in the portion of the body part is determined, the determination comprising utilizing the X-ray image.

In a second acquiring step 130, also referred to as step c), at least one ultrasonic image comprising a part of a body feature with the ultrasonic probe is acquired, the acquiring 130 comprising acquiring 140 an ultrasonic image of the at least one ultrasonic image at a later time than a time of acquisition of the X-ray image.

In a second determining step 150, also referred to as step g), second geometrical positional information of the ultrasonic probe 20 in the body part at the later time is determined, comprising utilizing the first geometrical positional information and the at least one ultrasonic image comprising the part of the body feature.

In an optional outputting step 160, also referred to as step i), data representative of the second geometrical positional information of the ultrasonic probe is output.

According to an example, step c) comprises acquiring at least two ultrasonic images comprising the part of the body feature with the ultrasonic probe. In this example, step c) further comprises acquiring 170 an ultrasonic image at substantially the same time as the time of acquisition of the X-ray image of the portion of the body part.

In an example, step c) comprises acquiring at least two ultrasonic images comprising the part of the body feature with the ultrasonic probe, and in this example step c) further comprises acquiring an ultrasonic image at substantially the same position as a position of the ultrasonic probe when the X-ray image of the portion of the body part was acquired.

According to an example, the method comprises: acquiring 180, also referred to as step h), a second X-ray image of the portion of the body part within which the ultrasonic probe is positioned if a threshold has been exceeded as a function of the first geometrical positional information and the second geometrical positional information.

According to an example, the method comprises: determining 190, also referred to as step d), at least one position of the ultrasonic probe relative to at least one position of the part of the body feature, utilizing the at least one ultrasonic image. In this example, step g) comprises utilizing 200 the at least one position of the ultrasonic probe relative to the at least one position of the part of the body feature.

According to an example, the method comprises: determining 210, also referred to as step e), segmented data of the part of the body feature using model based segmentation, utilizing the at least one ultrasonic image comprising the part of the body feature. In this example, step g) comprises utilizing 220 the segmented data of the part of the body feature.

According to an example, the method comprises: determining 230, also referred to as step f), a position of the part of the body feature as a reference position, utilizing the at least one ultrasonic image comprising the part of the body feature. In this example, step g) comprises utilizing 240 the reference position of the part of the body feature.

In an example, there is provided a method for tracking the position of an ultrasonic probe in a body part, comprising: providing an X-ray image of a portion of a body part within which an ultrasonic probe was positioned; determining first geometrical positional information of the ultrasonic probe in the portion of the body part, comprising utilizing the X-ray image; providing at least one ultrasonic image comprising a part of a body feature, wherein the at least one ultrasonic image was acquired by the ultrasonic probe and wherein an ultrasonic image of the at least one ultrasonic image was acquired at a later time than a time of acquisition of the X-ray image of the portion of the body part; determining second geometrical positional information of the ultrasonic probe in the body part at the later time, comprising utilizing the first geometrical positional information and the at least one ultrasonic image comprising the part of the body feature; and outputting of data representative of the second geometrical positional information of the ultrasonic probe.

Figure 4:
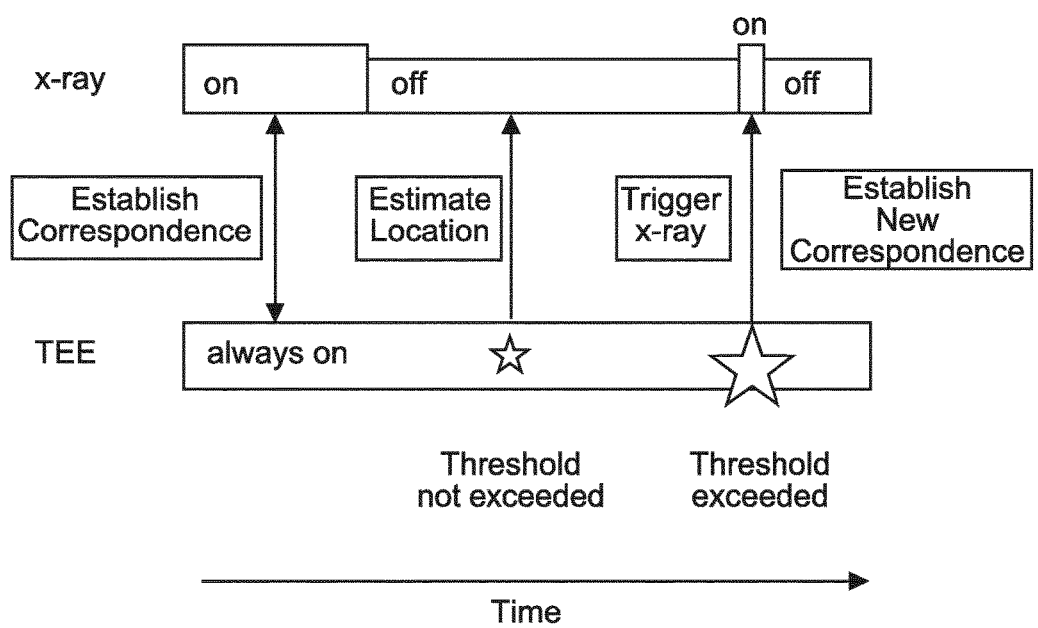
FIG. 4 shows an example of a workflow for tracking the position of an ultrasonic probe in a body part.

FIG. 4 shows a detailed workflow for tracking an ultrasonic probe in a body part. In summary, from an initial X-ray within which a TEE probe is located, correspondence between the TEE probe and the 3D volume of the X-ray unit is established by registering the TEE probe in the X-ray image. In other words, the TEE probe is located within the global space of the X-ray unit and is located within the anatomical space of the patient. When the X-ray unit is turned off, the TEE image feed is continuously segmented to estimate the new TEE probe location. For the case when a movement threshold has not been exceeded, which in an example can relate to small TEE probe movements, the estimated location is shown on the X-ray image. For the case when a movement threshold has been exceeded, which in an example can relate to large TEE probe movements, a new X-ray image may be triggered to measure the current probe position. The TEE probe can be localized in the X-ray image, and the ultrasound image can be overlaid on the X-ray image along with the position of the TEE probe, and annotations (e.g. markers ellipses) or a heart segmentation can also be overlaid on the X-ray image.

To summarize the above in a different manner:
1. The ultrasonic probe is localized in the X-ray image, through 2D-3D registration. The 2D-3D image registration provides the position and orientation of the probe in the X-ray image.
2. The part of the body feature, for example the heart, is segmented in the ultrasound image. The segmentation of the ultrasound image provides the outlines of the heart in the ultrasound volume.
3. From the 2D-3D registration of the probe in the X-ray image, the ultrasound volume being imaged by the ultrasound probe is known and can be located in the X-ray image. In this manner, contours of the heart, for example, can be drawn on top of the X-ray image. The above summary can be explained in slightly more detail as follows:
1. For localizing the probe in the x-ray using 2D-3D registration, a 3D model of the probe is known (e.g. from acquiring a nano-CT image). Then, for a given estimate of the probe orientation, a projection of the model, the so-called digitally reconstructed radiograph (DRR), is compared to the actual one or more X-ray images in which the probe should be localized. This process is repeated for several iterations in which the similarity between the DDR and the X-ray image is evaluated using an image comparison metric. The degrees of freedom (translation and rotation) are adjusted to best match the DDR with the X-ray image(s). In other words, the parameters of the position and orientation are optimized by maximizing the image similarity metric between DDR and X-ray image(s). The registration process is discussed in detail in a paper by Gao et al: Registration of 3D trans-esophageal echocardiography to X-ray fluoroscopy using image-based probe tracking, Medical Image Analysis 16 (2012) 38-49.
2. Model-based segmentation of for example the heart in the ultrasound image comprises a mean model, e.g. a triangular mesh consisting of N points and T triangles connecting the points. The initial shape describes for example an average or typical shape. The model is then adapted to an image in several steps. First, the general position (for example the center-of-gravity) and orientation are determined, and the mesh is placed accordingly in the image. During model training each triangle had learned which specific image features it should search for. During adaptation, each triangle then searches for these image features, resulting in a set of attracting forces (from which the so-called external energy is derived). Based on this external energy, the model is successively adapted by estimating parameters of global or regional affine transformations (the energy is minimized). In a final step, local deformations are allowed based on the external forces. At the same time, a so-called internal energy penalizes too large deviations from the mean shape. After multiple iterations, the shape of the mesh has been adapted to the image. Because it is known which mesh parts belong to which anatomical structures, this adds anatomical context to the image. A segmentation algorithm, applied to CT images but applied here to ultrasound images, is discussed in detail in the paper by Ecabert et al., Automatic Model-Based Segmentation of the Heart in CT Images, IEEE Transactions on Medical Imaging, Vol. 27, No. 9, September 2008, 1189-1201.
3. In step 2, the anatomical context is established locally in the ultrasound image. Because from step 1, the relationship between the ultrasound probe (and thus the coordinate system of the ultrasound image) and the global space (i.e., also the X-ray image) is known, the anatomical context (e.g. the segmentation mesh or special landmarks) can be displayed on top of the X-ray image.

In more detail, and with reference to FIG. 4, the system used to track the ultrasonic probe comprises an X-ray unit and a transoesophageal echo (TEE) probe. The 3D object (e.g. heart of the patient) between the X-ray source and the detector is intrinsically converted from 3D space to the projected 2D X-ray image by absorption along the radiation rays. The TEE probe is within the 3D volume and thus visible in the X-ray image. With an image processing algorithm, the TEE probe can be automatically detected. This way, the position and even orientation (using 2D-3D registration) of the TEE probe in the 3D volume of the X-ray unit can be determined. Here, it is described that the position and orientation of the TEE probe can be determined with reference to the X-ray unit, this however also means that the position and orientation can be determined with respect to the reference coordinates of the room within which the X-ray unit is housed. In this manner, the x, y, and z coordinates of the TEE probe can be determined, as well as the angular direction of a longitudinal axis of the TEE probe and the rotational angle of the TEE probe around that axis. In an example, the orientation comprises the three rotation angles (Euler angles or roll-pitch-yaw angles) to align the ultrasonic probe coordinate system with the X-ray image acquisition unit or coordinate system of the medical table. In other words, the reference coordinates of the TEE probe can be determined as well as where it is pointing and its axis rotational characteristic at that position determined.

By acquiring a TEE ultrasonic image at the same time as the X-ray image a transformation matrix $T_{TEE,Xvol}$ from the TEE image into the 3D volume of the X-ray unit can be determined. In this transformation, other known artificial transformations, such as a user-defined rotation around the z axis, so-called "scan angle" or seek angle, are included. Thus, it is known where in the X-ray unit volume the TEE image voxels are located. Using this information, the 3D TEE data can be projected onto the X-ray image such that any point of the 3D TEE image can be displayed at the correct position in the 2D projection X-ray image. Mathematically, this is expressed by a 2×3 projection matrix "P" and a 2D shift vector "$s_p$". Thus, any point "a" of the 3D coordinate system is projected onto a point "b" in the 2D coordinate system as b=P a+$s_p$. In other words, by determining a location and orientation of the TEE probe, from an X-ray image, whilst at the same time acquiring an ultrasonic image with the TEE probe, enables global and anatomical contextual and spatial information to be determined through mapping the acoustic image onto the X-ray image.

This is used, for example, to select landmarks in the 3D TEE image and project them onto the 2D X-ray image, or to segment the heart in the 3D TEE image and then overlay the segmentation results onto the 2D X-ray image. Regarding this method, the co-registration may need to be maintained over time, i.e., the probe may need to be continuously tracked to keep $T_{TEE,Xvol}$ up-to-date. If tracking can be performed without X-ray, the X-ray dosage can be reduced.

Therefore, the workflow for tracking an ultrasonic probe in a body part proceeds as follows:
1. Start at an instant at which an X-ray image and a TEE image are acquired.
2. Detect the heart in the TEE image and thus also in global space (using $T_{TEE,Xvol}$), thereby enabling the position of the heart to be determined.
3. For later instants without X-ray image data, use determined heart position as reference.
4. Detect TEE probe movement from the segmentation result of the TEE image only.
5. Use the detected TEE probe movement to
   a. Give an estimation of the current TEE probe position (without acquiring an X-ray image)
   b. If the detected TEE probe movement is above a certain threshold, trigger the acquisition of a new X-ray image to determine the absolute new position of the TEE probe.
   c. Virtually display the tracked TEE probe on the static X-ray image by using a 3D model of the TEE probe.

The heart is continuously segmented in the TEE images using model-based segmentation, see for example Ecabert, Oliver, et al. as referenced above. The segmentation, for example, adapts a mesh model to the TEE image. The mesh contains $N_P$ points and $N_T$ triangles. Because the mesh structure does not change, corresponding points between the different segmentation results are known.

The TEE image is always acquired relative to the TEE probe location and orientation, in terms of its positional coordinates and angular pointing direction and angular position around the TEE probe axis. Thus, if the position of the heart in the TEE image changes this may be caused either if the heart itself moves (beating, breathing), or if the TEE probe location or orientation has changed.

Intrinsic heart motion may be excluded, for example, by analyzing a consistent heart phase, such as end-systole. This information can be derived from the available ECG signal, or also from the segmentation result (e.g. when looking at the chamber volumes). Because breathing shifts the complete thorax including the probe, the relative position of the probe to the heart is affected only little. Alternatively, if needed, breathing can be detected without X-ray, for example, with a 'respiration belt' similarly as used with MR imaging. Then, from the remaining shift/rotation of the heart in the TEE image, a change in TEE probe translation and orientation is estimated as follows:

The TEE probe location is known at a time $t_0$ from an X-ray image, at which also a 3D TEE image $I_0$ is acquired. The probe location in 3D image space is $x_0$. The position of the heart in the image is described by the segmented mesh $M_0$.

At a later time $t_1$, a TEE image $I_1$ is acquired, but no X-ray need be acquired. The new probe location in 3D TEE space of $I_1$ is $x_1$. The new position of the heart in the image $I_1$ is described by the segmented mesh $M_1$.

The transformation matrix $T_{1,0}$ between the heart positions $M_1$ and $M_0$ is estimated. For example, a rigid transformation between the corresponding points in $M_1$ and $M_0$ can be calculated. Thus $T_{1,0}$ transforms points given in the image coordinates of $I_1$ to corresponding points in $I_0$.

The probe location $x_1$ from $t_1$ is transformed to the original image space in $I_0$ as $x_1'=T_{1,0}x_1$.

Then the difference d to the original position $x_0$ is calculated.

The new position $x_1'$ and the shift d that are known in the TEE image coordinate system of $I_0$ can be transformed to the 3D volume coordinate system, of the X-ray unit, using the known $T_{TEE,Xvol}$ from $t_0$. This way, the new 3D coordinates and the probe shift in the volume coordinates are known.

In other words, when no live X-ray is available, with appropriate considerations the anatomical heart position can be assumed to be fixed, and on the basis of this assumption TEE image data is used to estimate the TEE probe shift and/or rotation.

Figure 5:
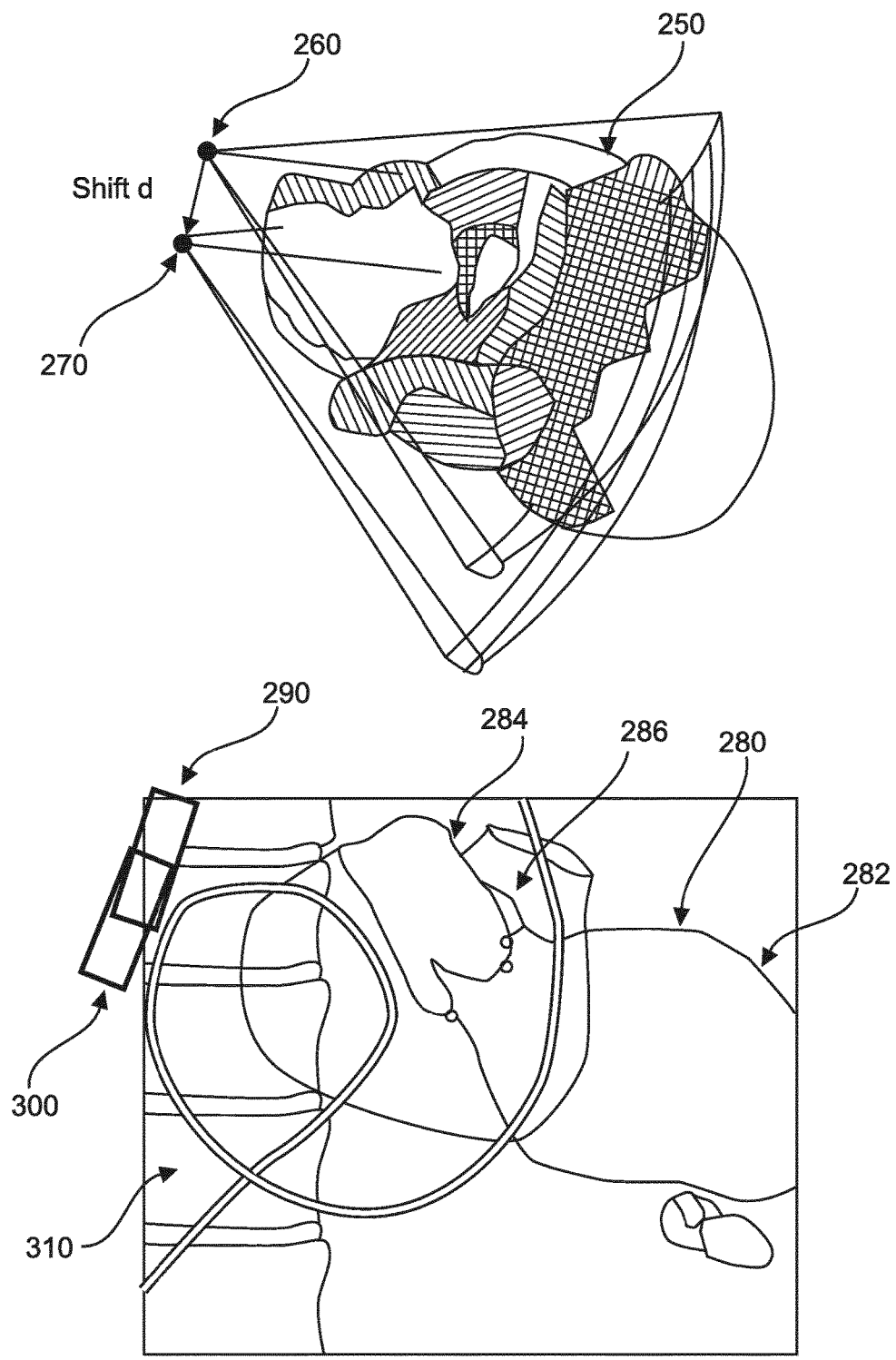
FIG. 5 shows on the left a schematic representation of ultrasonic probe positions relative to a model of a heart, and on the right a schematic representation of segmented ultrasonic image data of the heart superimposed onto an X-ray image where the ultrasonic probe positions are shown.
Figure 6:
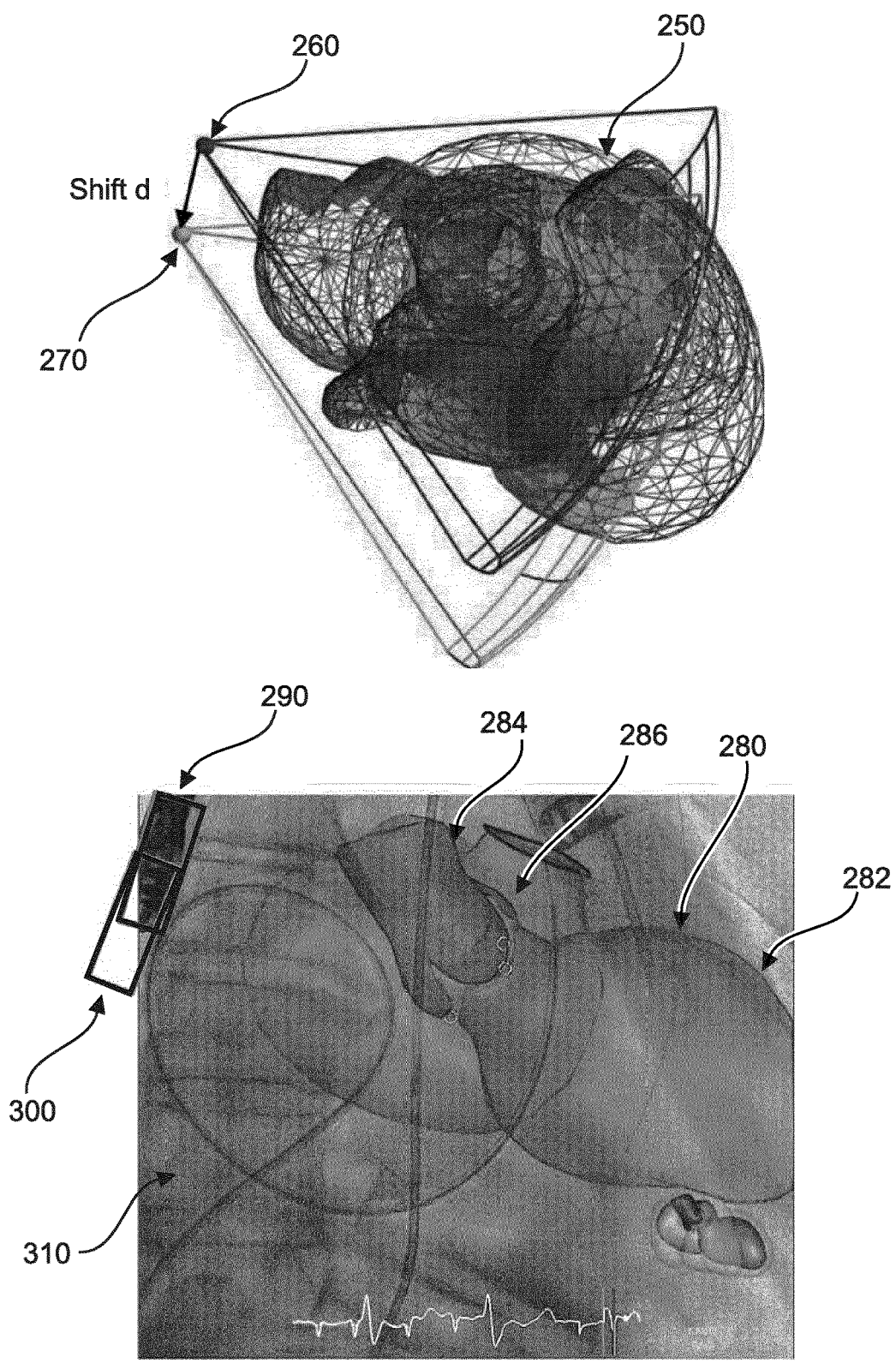
FIG. 6 shows the same information as that shown in FIG. 5, where schematic representations are replaced by image data.

FIG. 5 and FIG. 6 show a shift in the probe position in the left hand images, and an estimation of the TEE probe location displayed as an overlay onto an X-ray image in the right hand images. In the left hand image of FIGS. 5 and 6, the TEE probe position relative to the heart model 250 at the time of the last X-ray is shown as position 260. The TEE probe has then moved. With no further X-ray needing to be taken, from the segmentation of the heart in a new TEE image, the new probe location 270 and the shift d between the two locations 260 and 270 can be estimated. In the left had images of FIGS. 5 and 6 the new TEE probe location 270 is again shown relative to the heart model 250. In the right hand images of FIGS. 5 and 6, TEE image segmentation of the heart 280 is shown as an overlay onto an X-ray image. The heart 280 has been segmented into a number of regions, some of which are identified as segments 282, 284 and 286. In the X-ray image, a number of the patient's vertebra are shown 310. In the right hand image, the TEE probe position is shown in the upper left part of the image. At the time of the last X-ray image, the position of the TEE probe is indicated as position 290, and the new estimated location at a later time derived from the segmented TEE imagery is indicated as 300. If the shift length ldl exceeds a certain threshold $d_{thresh}$ acquisition of a new X-ray image can be automatically triggered. The method therefore provides a good compromise between dose exposure and tracking accuracy.

It will be appreciated that while the above workflow relates to model-based segmentation of a 3D volume, it is possible to detect shifts from other ultrasound images. For example, images can be acquired in x-plane mode, i.e. two orthogonal ultrasound slices are recorded. With changes in the position of the heart tracked across such images, an updated probe location can then be estimated and displayed.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus (i.e., system and workstation). The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for tracking a position of an ultrasonic probe, the system comprising:
   an ultrasonic probe configured to acquire at least one ultrasonic image of a part of a body feature when positioned in a body part;
   an X-ray image acquisition unit configured to acquire an X-ray image of a portion of the body part in which the ultrasonic probe is positioned; and
   a processor programmed to determine first geometrical positional information indicating a first position of the ultrasonic probe in the body part utilizing the X-ray image, and to determine second geometrical positional information indicating a second position of the ultrasonic probe in the body part at a later time, subsequent to a time of acquisition of the X-ray image of the portion of the body part, utilizing the first geometrical positional information and the at least one ultrasonic image of the part of the body feature acquired at the later time.

2. The system according to claim 1, wherein the at least one ultrasonic image is to be acquired at the same time as the time of acquisition of the X-ray image of the portion of the body part.

3. The system according to claim 1, wherein the processor is further programmed to determine when a threshold value has been exceeded as a function of the first geometrical positional information and the second geometrical positional information, and
wherein the X-ray image acquisition unit is further configured to acquire a second X-ray image of the portion of the body part in which the ultrasonic probe is positioned when the processor determines that the threshold value has been exceeded.

4. The system according to claim 1, wherein the processor is further programmed to determine at least one position of the ultrasonic probe relative to at least one position of the part of the body feature utilizing the at least one ultrasonic image, and to determine the second geometrical positional information of the ultrasonic probe utilizing the at least one position of the ultrasonic probe relative to the at least one position of the part of the body feature.

5. The system according to claim 1, wherein the processor is further programmed to determine segmented data of the part of the body feature using model based segmentation utilizing the at least one ultrasonic image of the part of the body feature, and to determine the second geometrical positional information of the ultrasonic probe utilizing the segmented data of the part of the body feature.

6. The system according to claim 1, wherein the processor is programmed to determine a position of the part of the body feature as a reference position utilizing the at least one ultrasonic image of the part of the body feature, and to determine the second geometrical positional information of the ultrasonic probe utilizing the reference position of the part of the body feature.

7. The system according to claim 1, wherein the processor is further programmed to determine the first geometrical positional information of the ultrasonic probe in the body part utilizing a three dimensional model of the ultrasonic probe.

8. The system according to claim 7, wherein the processor is further programmed to compare a projection of the three dimensional model of the ultrasonic probe with the X-ray image.

9. The system according to claim 7, wherein the processor is further programmed to iteratively determine a similarity between the three dimensional model and the X-ray image utilizing an image comparison metric.

10. The system according to claim 9, wherein the processor is further programmed to optimize at least one of a position and an orientation of the three dimensional model.

11. The system according to claim 7, wherein the processor is further programmed to compare the three dimensional model with the X-ray image by at least one of adjusting at least one translational degree of freedom of the three dimensional model and adjusting at least one rotational degree of freedom of the three dimensional model.

12. A workstation for tracking the position of an ultrasonic probe positioned in a body part, the workstation comprising:
at least one input unit configured to provide an X-ray image of a portion of the body part and at least one ultrasonic image of a part of a body feature; and
a processor programmed to determine first geometrical positional information indicating a first position of the ultrasonic probe in the body part utilizing the X-ray image,
wherein the at least one ultrasonic image is acquired by the ultrasonic probe positioned in the body part at a later time subsequent to a time of acquisition of the X-ray image of the portion of the body part, and
wherein, the processor is further programmed to determine second geometrical positional information indicating a second position of the ultrasonic probe in the body part corresponding to the later time utilizing the first geometrical positional information and the at least one ultrasonic image of the part of the body feature.

13. A method for tracking a position of an ultrasonic probe positioned in a body part, the method comprising:
a) acquiring an X-ray image of at least a portion of the body part in which ultrasonic probe is positioned;
b) determining first geometrical positional information indicating a first position of the ultrasonic probe in the portion of the body part utilizing the X-ray image;
c) acquiring an ultrasonic image of a part of a body feature using the ultrasonic probe at a later time after acquiring the X-ray image; and
d) determining second geometrical positional information indicating a second position of the ultrasonic probe in the body part at the later time utilizing the first geometrical positional information and the ultrasonic image of the part of the body feature.

14. A computer program product including instructions, executable by a processor, for carrying out the method for tracking the position of the ultrasonic probe in the body part, according to claim 13.

15. The system of claim 1, wherein the at least one ultrasonic image is to be acquired at the later time subsequent to the time of acquisition of the X-ray image of the portion of the body part.

16. The system of claim 1, wherein the processor determines the second geometrical positional information of the ultrasonic probe without the X-ray image acquisition unit acquiring another X-ray image of the portion of the body part in which the ultrasonic probe is positioned.

* * * * *